United States Patent [19]
Becker

[11] Patent Number: 6,063,250
[45] Date of Patent: May 16, 2000

[54] RUNNING TANK ASSEMBLY FOR ELECTROPHORESIS

[75] Inventor: Robert G. Becker, Northridge, Calif.

[73] Assignee: C.C. Imex, San Diego, Calif.

[21] Appl. No.: 09/079,342

[22] Filed: May 15, 1998

[51] Int. Cl.[7] .................................................. G01N 27/26
[52] U.S. Cl. ........................ 204/450; 204/466; 204/600; 204/616
[58] Field of Search .................................. 204/405, 456, 204/466, 600, 606, 616

[56] References Cited

U.S. PATENT DOCUMENTS

| | | | |
|---|---|---|---|
| 3,616,456 | 10/1971 | Valmet ..................................... | 204/299 |
| 3,839,184 | 10/1974 | Richter ..................................... | 204/299 |
| 3,873,433 | 3/1975 | Seidel et al. ......................... | 204/180 G |
| 4,164,464 | 8/1979 | Allington et al. .................... | 204/299 R |
| 4,284,491 | 8/1981 | Vesterberg .............................. | 204/606 |
| 4,310,408 | 1/1982 | Rose et al. .............................. | 204/301 |
| 4,415,426 | 11/1983 | Hsu et al. ............................. | 204/290 R |
| 4,576,702 | 3/1986 | Peck et al. ............................. | 204/299 R |
| 4,752,372 | 6/1988 | Rhodes et al. ........................ | 204/299 R |
| 5,405,520 | 4/1995 | Helfer .................................. | 204/299 R |
| 5,407,552 | 4/1995 | Lebacq ................................ | 204/299 R |
| 5,582,702 | 12/1996 | Cabilly et al. ......................... | 204/456 |
| B1 4,164,464 | 5/1992 | Allington et al. .................... | 204/299 R |

OTHER PUBLICATIONS

Brochure: Mupid–21 Mini–Gel Electrophoresis Unit–For DNA, RNA, & Proteins, Cosmo Bio Co., Ltd., Tokyo, Japan. 1997.

*Primary Examiner*—Jill Warden
*Assistant Examiner*—Alex Noguerola
*Attorney, Agent, or Firm*—John L. Rogitz

[57] ABSTRACT

An electrophoresis running tank assembly includes a running tank and a power supply holder that is integral to the running tank. A lid with two pins protruding from it can be engaged with the running tank with the pins extending through holes in the power supply holder. A contact is positioned in each hole, and the contacts are electrically connected to an electrophoresis electrode in the running tank. When a power supply is advanced into the power supply holder and the lid is properly positioned on the running tank, the pins on the lid mate with receptacles of the power supply, thereby establishing a connection between the power supply receptacles and the contacts in the holes and, hence, the electrophoresis electrode.

16 Claims, 3 Drawing Sheets

RUNNING TANK ASSEMBLY FOR ELECTROPHORESIS

FIELD OF THE INVENTION

The present invention relates generally to electrophoresis, and more particularly to running tank assemblies for electrophoresis.

BACKGROUND

Electrophoresis is used for a large number of applications. As an example of but one application, DNA sequencing to determine the genetic composition of a sample of DNA can be undertaken using electrophoresis.

Many existing electrophoresis applications are undertaken using so-called running tanks, in which a sample-containing gel is disposed in an electrophoresis chamber in the tank. Electric current is then applied to the gel by means of an electrode in the tank to cause electrophoresis of the sample.

For safety reasons, the electrophoresis chamber preferably is covered by a lid when energized. To ensure that the lid covers the electrophoresis chamber prior to energizing the gel, interlocks have been provided to break the electric current path between an electrophoresis power supply and the tank electrode when the lid is not properly engaged with the running tank.

As one example of such an interlock, microswitches have been provided on the top edge of running tanks, and the microswitches are closed by a lid when the lid is placed on the tank, thereby completing the electrical circuit between the tank electrode and the power supply. Unfortunately, the tank electrode can be energized anytime the microswitches are depressed, whether by a lid or by a substitute mechanism. Thus, the interlock easily can be defeated.

An alternative interlock is disclosed in U.S. Pat. No. 5,405,520, which discloses a plug that is completely recessed into a running tank cover. The cover is formed with a slot that extends to the plug, and a switch on the running tank is advanced into the slot against the plug when the lid is lowered down onto the tank. When the switch contacts the plug, an electrical circuit is established to the running tank electrode. However, the switch can be "made" by contact with components other than the plug in the cover; consequently, the interlock can be easily defeated.

Still another alternate interlock is exemplified in a device marketed under the trade name "Mupid-21" by Cosmo Bio Ltd. of Japan. In the Mupid-21 device, a running tank cover has a vertical wall and a plug protruding from a front side of the wall. The rear end of the plug is exposed at a rear side of the wall. To engage the lid with a running tank, the lid is lowered onto the tank with the vertical wall of the lid disposed flush against an inside surface of a wall of a power supply bay that is formed as part of the tank. The wall of the power supply bay holds a contact that is connected to the running tank electrode, such that the rear end of the plug wipes the contact when the lid is slid onto the tank. Then, a power supply having a receptacle is advanced into the bay until the plug mates with the receptacle, thereby completing the electrical circuit between the running tank electrode and the power supply.

It happens that a user of an electrophoresis apparatus might undertake many successive electrophoresis experiments over the course of a day, requiring the lid to be removed from the running tank between experiments to modify or replace the gel in the running tank. Unfortunately, the Mupid-21 design necessitates removing the power supply from the bay to remove the lid from the running tank, which users find cumbersome and time consuming. As recognized herein, however, it is possible to provide an electrophoresis running tank assembly which ensures that a power supply cannot be electrically connected to a running tank electrode without first covering the running tank with a lid, and which does not require the power supply to be removed from the assembly to remove the lid from the running tank.

Accordingly, it is an object of the present invention to provide an electrophoresis running tank assembly which prevents energizing a running tank electrode unless a lid is properly positioned on the running tank. Another object of the present invention is to provide an electrophoresis running tank assembly which permits removing the lid from the running tank without removing the power supply from the assembly. Still another object of the present invention is to provide an electrophoresis running tank assembly that is easy to use and cost effective to manufacture.

SUMMARY OF THE INVENTION

An electrophoresis assembly includes a running tank defining an electrophoresis chamber, and at least one conductor is disposed on the tank for conducting electric current to the chamber. A power supply holder is contiguous to the running tank. The power supply holder includes a rear holder wall defining at least one hole, and the power supply holder also defines a power supply bay. At least one electrically conductive contact is associated with the hole in the holder wall, with the contact being electrically connected to the conductor.

Further, a lid defines a cover plate and a rear lid wall depending downwardly from the cover plate. As intended by the present invention, the lid is selectively engageable with the running tank and the power supply holder such that the cover plate covers the electrophoresis chamber and the lid wall is adjacent to and indeed may be flush against the holder wall. At least one electrically conductive pin extends forwardly of the rear lid wall and is attached thereto. In accordance with principles discussed in detail below, the pin is configured for being closely received within the hole of the power supply holder for touching the contact when the lid is engaged with the running tank to cover the chamber. With this cooperation of structure, a power supply can be positioned in the power supply bay in electrical engagement with the pin to thereby establish a pathway for electrical communication from the power supply to the electrophoresis chamber.

In a preferred embodiment, the power supply snappingly engages the power supply holder. Consequently, when the lid is slid off of the power supply holder (and, hence, when the pins of the lid are disengaged with the power supply), the power supply remains disposed in the power supply holder, without requiring a person to hold the power supply while removing the lid. A person can, however, overcome the snapping engagement between the power supply and power supply holder by pulling the power supply away from the power supply using slight to moderate pulling force.

In another aspect, an apparatus for electrophoresis includes a running tank assembly defining at least one electrophoresis chamber and at least one hole. At least one contact is on the running tank assembly in electrical communication with the electrophoresis chamber. A lid includes at least one pin protruding therefrom and configured for being closely received within the hole while in electrical communication with the contact. The lid covers the electrophoresis chamber when the pin engages the contact.

In still another aspect, a method for electrophoresis is disclosed. The method includes providing a running tank assembly including at least one electrophoresis chamber and at least one contact in electrical communication with the chamber. A lid is provided which includes at least one pin. The method then envisions engaging the lid with the running tank assembly to cover the electrophoresis chamber by touching the pin to the contact. Next, the method requires electrically engaging at least one receptacle of a power supply with the pin to provide electrical current in the electrophoresis chamber.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
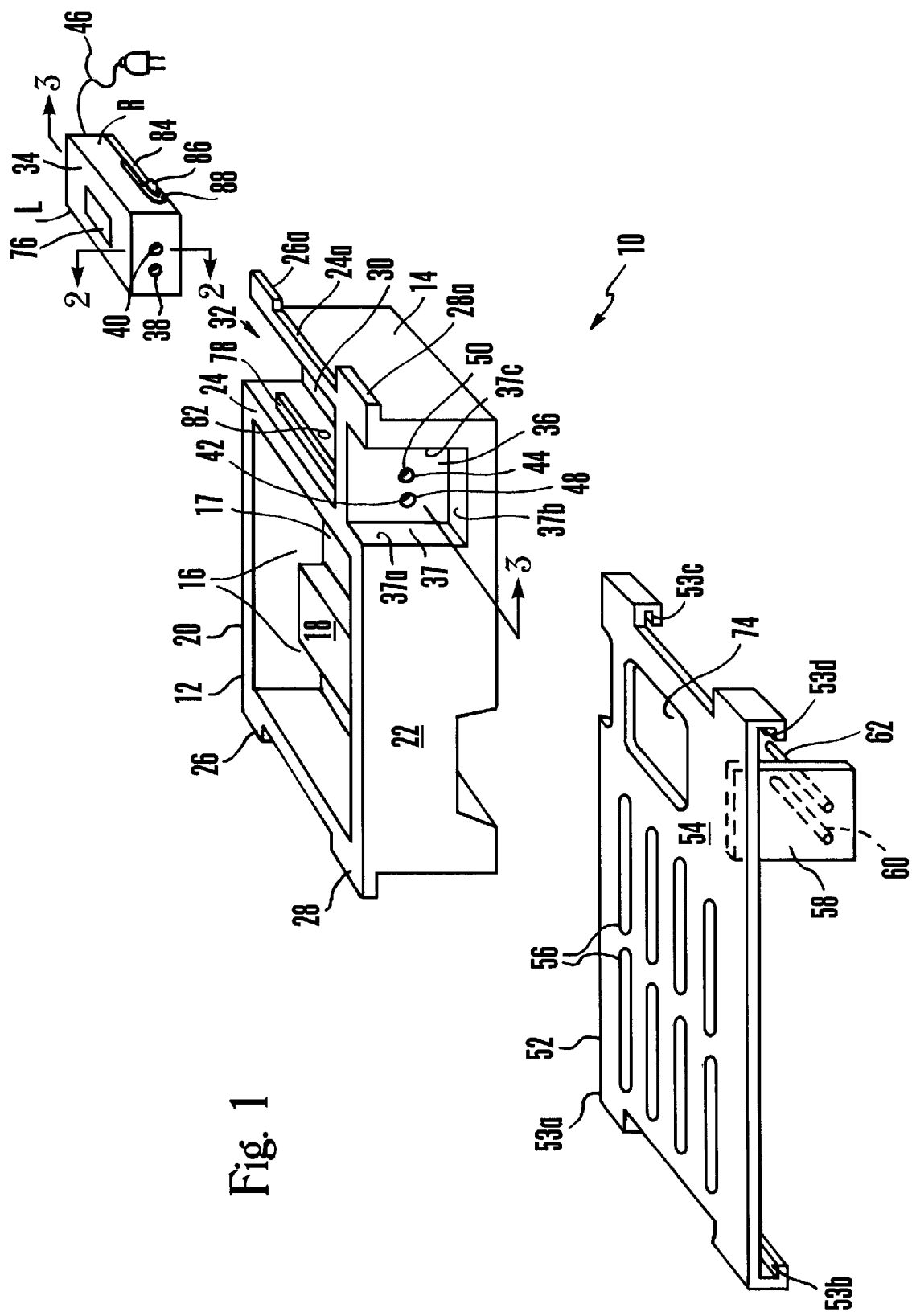
FIG. 1 is a perspective view of the electrophoresis running tank assembly, showing the components in an exploded relationship, with portions shown in phantom.

Referring initially to FIG. 1, a running tank assembly for electrophoresis is shown, generally designated 10. It is to be understood that FIG. 1 shows the assembly 10 in its intended upright orientation; accordingly, terms of orientation used herein, such as "vertical" and "horizontal", are referenced to the intended upright orientation of the assembly 10 shown in FIG. 1.

As shown, the assembly 10 includes a hollow plastic running tank 12 and a hollow plastic power supply holder 14 contiguous thereto. More preferably, the power supply holder 14 is made integrally with the running tank 12. The running tank 12 is configured for electrophoresis, and accordingly the running tank 12 defines one or more electrophoresis chambers 16 in electrical communication with one or more electrophoresis electrodes (only one electrode 17 shown in FIG. 1). A gel containing a sample of, e.g., DNA, can be disposed in the electrophoresis chamber 16 for electrophoresis of the sample in accordance with the present invention. If desired, a central raised ridge 18 can extend longitudinally in the chamber 16 from a front vertical wall 20 of the tank 12 to a rear vertical wall 22.

Furthermore, the tank 12 defines a rectangular upper edge 24, and front and rear left parallelepiped-shaped rails 26, 28 extend along the left side of the top edge 24 as shown.

Likewise, the power supply holder 14 defines an upper edge 24a, and front and rear right parallelepiped-shaped rails 26a, 28a extend along the right side of the top edge 24a of the power supply holder 14 as shown.

Turning more specifically to the power supply holder 14, the holder 14 defines a power supply bay 30, an open front end 32 into which a power supply 34 can be advanced, and a rear vertical wall 36 opposite the open front end 32. A pin cell 37 having walls 37a, 37b, 37c is established between the rear vertical wall 36 and the common rear wall 22 of the running tank 12/power supply holder 14. In the preferred embodiment, the power supply 34 includes left and right receptacles 38, 40, and the wall 36 of the power supply holder 14 likewise is formed with left and right holes 42, 44. It can be appreciated in reference to FIG. 1 that when the power supply 34 is fully advanced into the power supply bay 30, the left receptacle 38 is coaxial with and closely spaced from the left hole 42. Similarly, when the power supply 34 is fully advanced into the power supply bay 30, the right receptacle 40 is coaxial with and closely spaced from the right hole 44. It is to be understood that the power supply 34 can be energized from an electrical outlet by means of a cord 46 in accordance with conventional principles.

As disclosed in detail below, the power supply 34 snappingly engages the power supply holder 14 when the power supply 34 is advanced into the holder 14. The particularly preferred means by which this snapping engagement is undertaken is set forth more fully below. In any case, the snapping engagement holds the power supply 34 within the power supply bay 30 unless and until a person pulls the power supply 34 out of the bay 30 with a force that, while being relatively slight, nonetheless is sufficient to overcome the snapping engagement.

As also disclosed in detail below with reference to FIG. 2, respective left and right electrical contacts 48, 50 are associated with the left and right holes 42, 44 of the power supply holder 14. More particularly, each contact 48, 50 is arcuate in shape such that it partially or completely circumscribes the inner periphery of its respective hole 42, 44. It is to be understood that the left and right electrical contacts 48, 50 are electrically connected to one or more of the electrophoresis electrodes 17 in the running tank 12.

A plastic, preferably transparent lid 52 can be engaged with the running tank 12 and power supply holder 14 to cover the electrophoresis chamber 16 and to interconnect the receptacles 38, 40 of the power supply 34 with the contacts 48, 50 of the power supply holder 14. More specifically, a top plate 54 of the lid 52 is formed with front and rear left U-shaped channels 53a, 53b, and the lid 52 can be slid onto the running tank 12 such that the front and rear channels 53a, 53b surroundingly engage the front and rear left rails 26, 28. Also, the top plate 54 is formed with front and rear right U-shaped channels 53c, 53d, and the lid 52 can be slid onto the running tank 12 such that the front and rear right channels 53c, 53d surroundingly engage the front and rear right rails 26a, 28a. With this structure, the lid 52 is held securely onto the running tank 12 and the power supply holder 14.

As shown, the lid 52 includes a top plate 54 that is formed with two rows of transversely oriented, elongated viewing slots 56. Each viewing slot 56 is sufficiently small such that a human finger cannot protrude through the slot. On the other hand, the viewing slots permit a person to view the interior of the electrophoresis chamber 16 when the lid 52 is on the tank 12. As recognized herein, conventional running tank lids without slots can become fouled with steam or condensation during electrophoresis, thereby preventing a person from inspecting the chamber 16 during electrophoresis with the lid in place. Owing to the slots 56, the present lid 52 overcomes this drawback. Further, the slots 56 promote heat exchange across the lid 52, so that the temperature of the running buffer advantageously is lower than it would be otherwise.

A lid wall 58 depends vertically downwardly from the top plate 54. Left and right electrically conductive pins 60, 62 are attached to the lid wall 58, and the pins 60, 62 protrude forwardly and horizontally from the wall 58. In accordance with the present invention, the pins 60, 62 are configured for advancing into and being closely received by the holes 42, 44 of the power supply holder 14 and the receptacles 38, 40 of the power supply 34. Stated differently, the lid 52 is engaged with the running tank 12 and power supply holder 14 by advancing the lid forwardly in the horizontal plane until the pins 60, 62 extend through the holes 42, 44 with the lid wall 58 flush against the vertical wall 36 of the power supply holder 14. The skilled artisan will appreciate that the pins 60, 62 accordingly establish part of the electrical path from the power supply 34 to the contacts 48, 50.

Figure 2:
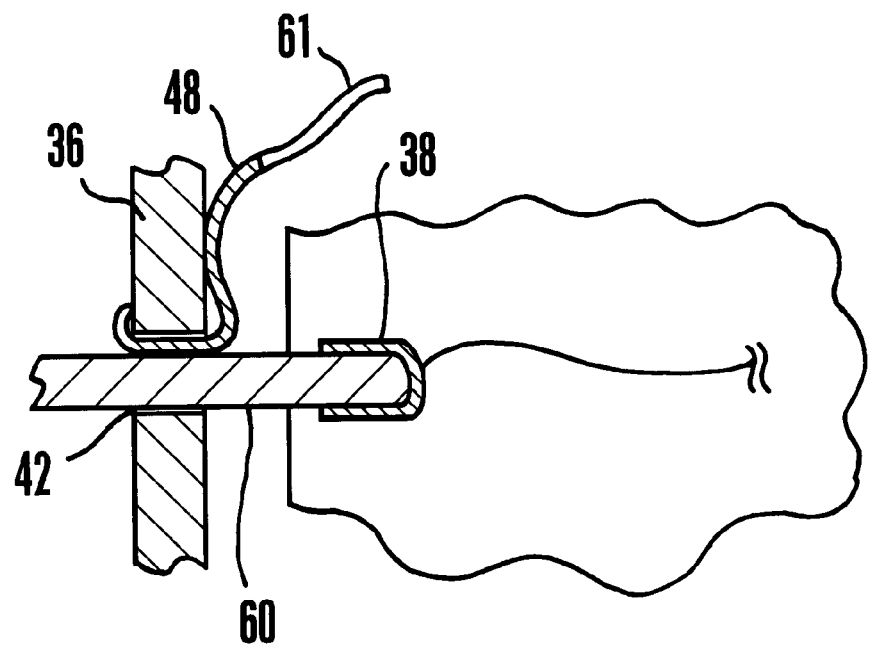
FIG. 2 is a cross-sectional view as would be seen along the line 2—2 in FIG. 1 with the components engaged with each other, showing the cooperation between the lid pin, the power supply holder connector, and the power supply receptacle, with portions cut away for clarity.

In brief cross-reference to FIGS. 1 and 2, when the pins 60, 62 extend horizontally through the holes 42, 44, the pins 60, 62 wipe against the contacts 48, 50 to thereby touch the contact and establish electrical contact with the contacts 48, 50. In turn, the contacts 48, 50 are connected to the electrophoresis electrodes via respective leads (only one lead 61 shown in FIG. 2). Desirably, the contacts 48, 50 are materially biased toward the center of their respective holes 42, 44, to ensure firm electrical contact between the contacts 48, 50 and the pins 60, 62. Consequently, when the power supply 34 is plugged into the pins 60, 62, an electrical circuit is established from the power supply 34, to the pins 60, 62, to the contacts 48, 50, and then via the leads or lead 61 to the electrodes or electrode 17.

It may now be appreciated that owing to the cooperation of structure between the channels 53a–d and rails 26, 28, 26a, 28a, the lid 52 cannot be lifted off of the running tank 12, but must instead be slid off. Indeed, no corner of the lid 52 can be pried away from the running tank 12, owing to the cooperation of structure between the channels 53a–d and rails 26, 28, 26a, 28a. Since sliding the lid 52 off of the running tank 12 in turn disengages the pins 60, 62 from the electrical circuit, safety is promoted in that the power supply 34 is electrically disconnected from the electrode 17 when the running tank 12 is uncovered. Because of the cutout portions of the lid 52 between the left channels 53a and 53b and between the right channels 53c and 53d, the lid 52 need not be slid the full length of the tank, but instead can be lowered onto the tank such that the left channels 53a, 53b straddle the left rear rail 28 and the right channels 53c, 53d straddle the right rear rail 28a. Then, the lid 52 is slid horizontally forwardly on the tank 12 to effect the above-noted engagement.

It can be further appreciated that the primary function of the channels 53a–d and rails 26, 28, 26a, 28a is to hold the lid 52 onto the running tank 12, whereas the primary function of the pins 60, 62 is to complete the electrical path between the power supply 34 and the electrode 17. Consequently, the lid 52 establishes an interlock such that the electrophoresis chamber 16 cannot be energized from the power supply 34 unless the lid 52 is in its intended position, i.e., covering the chamber 16. With this structure, the lid 52 ensures that the chamber 16 is covered, for safety reasons, whenever the electrode 17 is energized.

However, the power supply 34 advantageously need not be removed from the power supply holder 14 to remove the lid 52 from the running tank 12. Indeed, owing to the snapping engagement of the power supply 34 with the holder 14, the power supply 34 conveniently remains in the bay 30 when the lid 52 is removed from the running tank 12, e.g., to temporarily inspect the interior of the running tank 12, unless a person happens to pull the power supply 34 out of the bay 30 while removing the lid 52. Of course, the above-noted safety features prevent the power supply 34 from energizing the electrode 17 when the lid 52 is removed from the running tank 12. Also, as the lid 52 is being slid onto the running tank 12 and the pins 60, 62 start to engage the contacts 48, 50, the pins 60, 62 advantageously are shielded to the touch by the lid 52, pin cell walls 37a–c, and power supply holder wall 36. In any case, the lid 52 and power supply 34 conveniently can be engaged with the running tank 12 in any order, i.e., lid 52 first or power supply 34 first, with the above-described safety interlock preventing access to an energized electrode 17 in either case.

Figure 3:
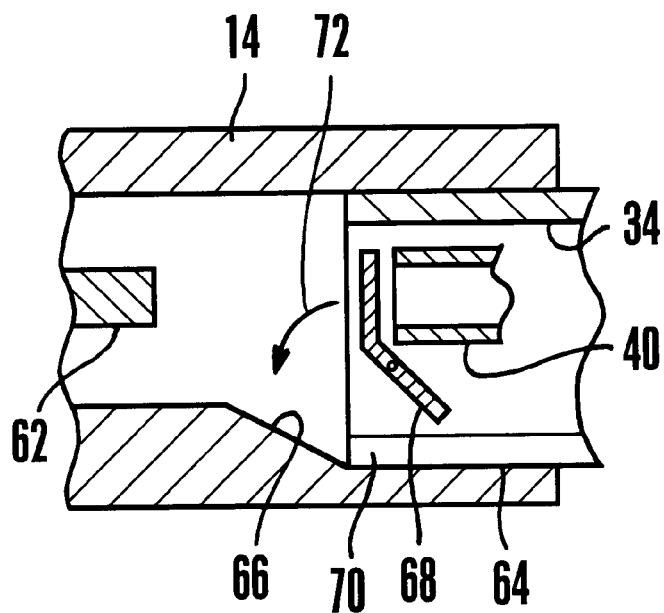
FIG. 3 is a cross-sectional view as would be seen along the line 3—3 in FIG. 1 with the power supply advanced toward, but not yet engaged with, the pins of the lid, showing the cooperation between the ramp on the power supply bay and the power supply gate, with portions cut away for clarity.

FIG. 3 illustrates additional details of the electrophoresis running tank assembly 10. More particularly, FIG. 3 shows that the power supply holder 14 defines a floor 64 of the power supply bay 30, and two ramps (only a single ramp 66 shown) rise upwardly from the floor 64. Each power supply receptacle 38, 40 is covered by a respective plastic gate (only the right gate 68 shown) that is pivotably mounted in the power supply 34. A slot 70 is formed in the power supply 34 directly beneath the gate 68, such that when the power supply 34 is advanced into the power supply holder 14, the ramp 66 is received in the slot 70, and the gate 68 rides on the ramp 66 to pivot in the direction indicated by the arrow 72.

The skilled artisan will appreciate that this pivoting of the gate 68 exposes the receptacle 40, such that the pin 62 can enter the receptacle 40. The gate 68 is spring biased to the position shown in FIG. 3, such that when the power supply 34 is removed from the power supply holder 14, the gate 68 pivots to cover the receptacle 40. It is to be understood that the left receptacle 38 of the power supply 34 is likewise covered and uncovered by a gate when the power supply 34 is disengaged and engaged with the power supply holder 14. It is to be further understood that the receptacles 38, 40 of the power supply 34 can be covered by other movable means that are actuated when the power supply 34 is engaged with the power supply bay 30.

As recognized by the present invention, power supply controls (not shown) are located in the power supply 34, and the user might desire to manipulate the controls. To facilitate this, the top plate 54 of the lid 52 can be formed with a cutout section 74. As can be appreciated in reference to FIG. 1, when the lid is engaged with the running tank 12/power supply holder 14, the cutout section 74 is located above a touch pad membrane 76 in the power supply 34. Accordingly, the membrane 76 can be manipulated through the cutout section 74 to operate the controls of the running tank assembly 10 without removing the lid 52 from the running tank 12.

As mentioned above, the power supply 34 snappingly engages the power supply holder 14 in the bay 30 thereof, such that a person can slide the lid. In the preferred embodiment, the structure for effecting this is as follows. Referring back to FIG. 1, the holder 14 can be formed with identical left and right elongated flanges 78 (only the left flange shown in the perspective of FIG. 1) that are spaced from the bottom floor 64 of the bay 30. Below each flange, near the wall 36 of the bay 30, a respective hemispherical indent 82 is formed (only the left indent shown in the perspective of FIG. 1).

The power supply 34 is formed with identical elongated left and right snap arms 84 (only the right snap arm shown in FIG. 1). The snap arms terminate in respective hemispherical detents 86 (only the right detent shown in FIG. 1), with the snap arms being materially biased such that the detents respectively protrude beyond the left and right sides "L" and "R" of the power supply 34. A respective cutout portion 813 (only the right cutout portion shown) is formed under each detent 86.

With the above-described combination of structure, the power supply 34 is slid into the bay 30 with the arms 84 sliding between the flanges 78 and the bottom 64 of the bay 30 and with the detents 86 riding against the sides of the bay 30. When the detents 86 ride against the sides of the bay 30, the arms 84 are pushed inwardly. When the power supply 34 has been fully advanced into the bay 30, the detents 86 are juxtaposed with the respective indents 82 and the arms 84 consequently snap outwardly to snappingly engage the detents 86 with the respective indents 82, thereby holding the power supply 34 in the power supply bay 30. A user can disengage the detents 86 from the indents 82 by exerting a mild pulling force on the power supply 34.

Figure 4:
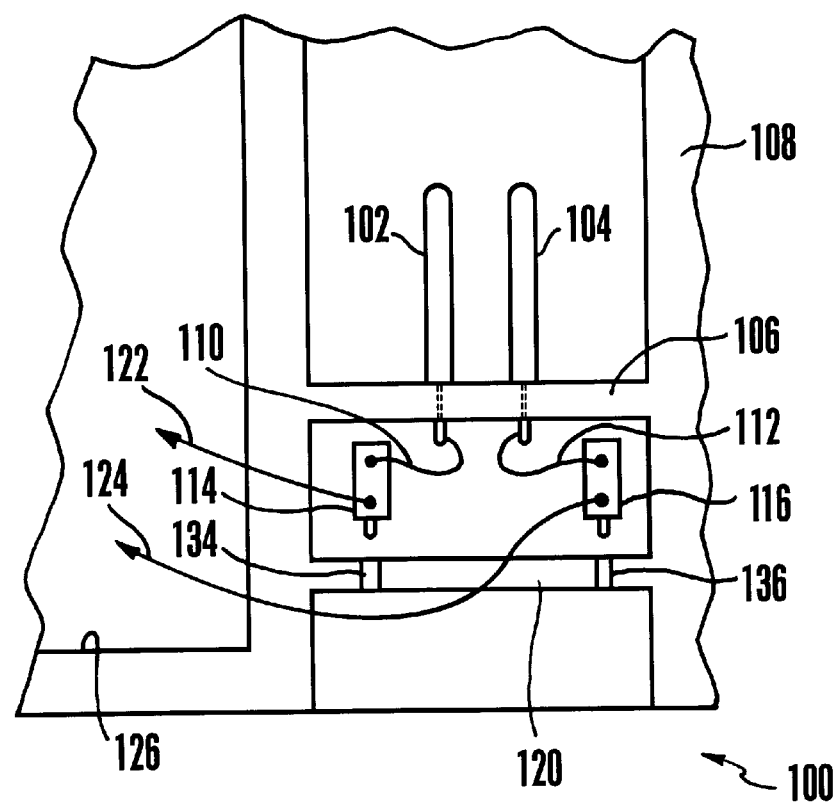
FIG. 4 is a top plan view of an alternate interlock structure, with portions broken away for clarity.
Figure 5:
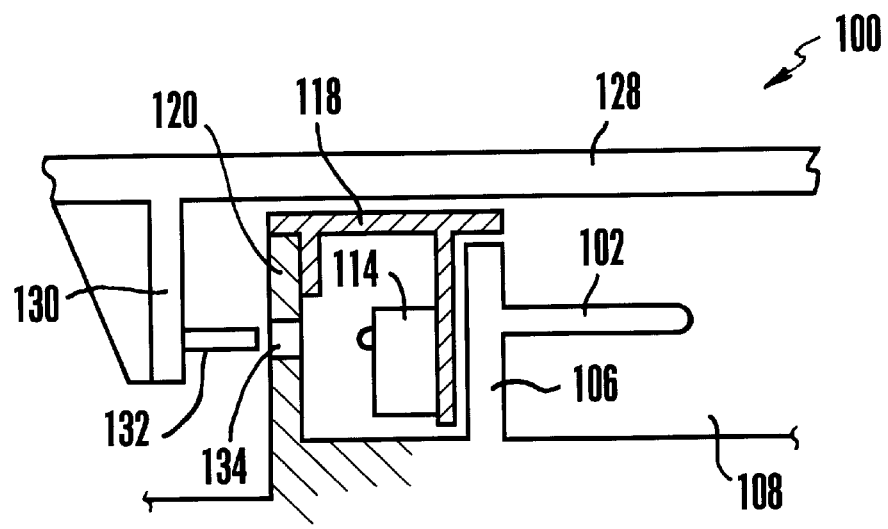
FIG. 5 is a partial cross-sectional elevational view of the alternate interlock structure shown in FIG. 4, with portions broken away for clarity.

FIGS. 4 and 5 show an alternate running tank assembly, generally designated 100, that is in all essential respects identical in configuration and operation to the assembly 10 shown in FIGS. 1–3, with the following exceptions. The safety interlock mechanism of the apparatus 100 includes two elongated metal prongs 102, 104 that are fixedly attached to a forward vertical wall 106 of a power supply holder 108 and that are configured for mating with the receptacles of a power supply (not shown in FIGS. 4 and 5). The prongs 102, 104 are electrically connected via respective leads 110, 112 to respective microswitches 114, 116 which, as can best be appreciated in reference to FIG. 5, are fixedly attached to a plastic insert 118 that is held between the forward vertical wall 106 and a rear vertical wall 120 of the power supply holder 108. In turn, once again referencing FIGS. 4 and 5, the microswitches 114, 116 are electrically connected, via respective leads 122, 124, to one or more conductors/electrodes in a running tank 126 of the apparatus 100.

A lid 128 is formed with a vertical wall 130, and two co-parallel rigid actuators (only one actuator 132 shown) protrude horizontally forwardly away from the wall 130 of the lid 128. The actuators 132 are received in respective holes 134, 136 that are formed in the rear vertical wall 120 of the power supply holder 108. When the lid 128 is slid forwardly onto the running tank 126/power supply holder 108 a sufficient amount, the actuators 132 abut respective microswitches 114, 116 to close the microswitches and thereby complete the electrical path between the prongs 102, 104 and the running tank electrodes/conductors. Accordingly, when the prongs 102, 104 are plugged into a power supply (not shown) that has been positioned in the power supply holder 108, the electrical circuit between the power supply and the running tank electrodes can be completed only when the lid 128 is properly engaged with the running tank 126 and power supply holder 108 to close the microswitches 114, 116.

While the particular RUNNING TANK ASSEMBLY FOR ELECTROPHORESIS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more".

What is claimed is:

1. An electrophoresis assembly, comprising:

at least one running tank defining at least one electrophoresis chamber;

at least one conductor disposed on the tank for conducting electric current for electrophoresis in the chamber;

at least one power supply holder contiguous to the running tank, the power supply holder including at least one rear holder wall defining at least one hole, the power supply holder defining at least one power supply bay;

at least one electrically conductive contact associated with the hole in the holder wall, the contact being electrically connected to the conductor;

at least one lid defining at least one cover plate and at least one rear lid wall depending downwardly therefrom, the lid being selectively engageable with the running tank and the power supply holder such that the cover plate covers the electrophoresis chamber; and at least one electrically conductive pin extending forwardly of the rear lid wall and attached thereto, the pin being configured for being closely received within the hole for touching the contact when the lid is engaged with the running tank to cover the chamber, wherein at least one power supply can be positioned in the power supply bay in electrical engagement with the pin to thereby establish a pathway for electrical communication from the power supply to the electrophoresis chamber, and wherein no pathway for electrical communication exists when the lid with pins is removed from the running tank.

2. The assembly of claim 1, wherein the power supply snappingly engages the power supply holder when engaged therewith.

3. The assembly of claim 1, further comprising a power supply.

4. The assembly of claim 1, wherein the lid is formed with plural elongated viewing slots.

5. An apparatus for electrophoresis, comprising:

a running tank assembly defining at least one electrophoresis chamber and at least one hole;

at least one contact on the running tank assembly in electrical communication with the electrophoresis chamber; and a lid including at least one pin protruding therefrom and configured for being closely received within the hole while in electrical communication with the contact, the lid covering the electrophoresis chamber when the pin engages the contact, wherein the running tank assembly includes a running tank and at least one power supply holder contiguous to the running tank, the power supply holder including at least one rear vertical holder wall, the holder wall defining the least one hole, the power supply holder defining at least one power supply bay.

6. The apparatus of claim 5, further comprising at least one conductor disposed on the tank for conducting electric current to the electrophoresis chamber.

7. The apparatus of claim 6, wherein the contact is associated with the hole in the holder wall, the contact being electrically connected to the conductor.

8. The apparatus of claim 7, wherein the lid defines at least one cover plate and at least one rear lid wall depending downwardly therefrom, the lid being selectively engageable with the running tank and the power supply holder such that the cover plate covers the electrophoresis chamber and the lid wall is flush against the holder wall, the pin extending forwardly of the rear lid wall and attached thereto, the pin being configured for being closely received within the hole for touching the contact when the lid is engaged with the running tank to cover the chamber.

9. The apparatus of claim 8, further comprising at least one power supply positionable in the power supply bay in electrical engagement with the pin to thereby establish a pathway for electrical communication from the power supply to the electrophoresis chamber.

10. The apparatus of claim 9, wherein the power supply snappingly engages the power supply holder.

11. A method for electrophoresis, comprising the steps of:
providing a running tank assembly including at least one electrophoresis chamber and at least one contact in electrical communication therewith;
providing a lid including at least one pin;
engaging the lid with the running tank assembly to cover the electrophoresis chamber by touching the pin to the contact; and
electrically engaging at least one receptacle of a power supply with the pin to provide electrical current in the electrophoresis chamber, wherein the lid is formed with a vertically oriented lid wall, and the pin protrudes horizontally away from the lid wall.

12. The method of claim 11, wherein the running tank assembly is formed with at least one hole and the contact is positioned in the hole, and the pin is receivable in the hole.

13. The method of claim 12, further comprising the steps of disposing a gel in the electrophoresis chamber and depositing a DNA sample on the gel for undertaking DNA sequencing of the DNA sample.

14. The method of claim 11, further comprising the step of:
snappingly engaging the power supply with the running tank assembly to thereby hold the power supply in the assembly.

15. The method of claim 14, further comprising the step of biasing the gate to cover the receptacle.

16. The method of claim 11, further comprising the step of forming the lid with plural elongated viewing slots.

* * * * *